(12) United States Patent
Rees et al.

(10) Patent No.: US 10,874,448 B2
(45) Date of Patent: Dec. 29, 2020

(54) TOOL FOR USE WITH A FASTENER

(71) Applicant: LUNAR INNOVATION LIMITED, Cambridgeshire (GB)

(72) Inventors: Samuel Rees, Rotherham (GB); Vaughan Rimmer, Derby (GB); Susan Allison, Derby (GB)

(73) Assignee: LUNAR INNOVATION LIMITED, Cambridgeshire (GB)

( * ) Notice: Subject to any disclaimer, the term of this patent is extended or adjusted under 35 U.S.C. 154(b) by 0 days.

(21) Appl. No.: 15/775,525

(22) PCT Filed: Nov. 10, 2016

(86) PCT No.: PCT/GB2016/053520
§ 371 (c)(1),
(2) Date: May 11, 2018

(87) PCT Pub. No.: WO2017/081468
PCT Pub. Date: May 18, 2017

(65) Prior Publication Data
US 2018/0263676 A1    Sep. 20, 2018

(30) Foreign Application Priority Data

Nov. 11, 2015 (GB) .................................. 1519915.1

(51) Int. Cl.
*A61B 17/88* (2006.01)
*B25B 15/00* (2006.01)
*B25B 23/10* (2006.01)

(52) U.S. Cl.
CPC ........ *A61B 17/8888* (2013.01); *B25B 15/008* (2013.01); *B25B 23/108* (2013.01)

(58) Field of Classification Search
CPC ....... B25B 15/008; B25B 15/06; B25B 15/00; B25B 23/108; B25B 23/10; B25B 23/08;
(Continued)

(56) References Cited

U.S. PATENT DOCUMENTS

| 1,699,306 | A | * | 1/1929 | Millen | ................. | B25B 23/106 |
|           |   |   |        |        |                   | 81/443      |
| 3,604,487 | A | * | 9/1971 | Gilbert | ................ | A61B 17/861 |
|           |   |   |        |        |                   | 81/443      |

(Continued)

FOREIGN PATENT DOCUMENTS

GB        1122214        7/1968

OTHER PUBLICATIONS

International Search Report dated Feb. 17, 2017 issued in PCT International Patent Application No. PCT/GB2016/053520, 2 pp.

(Continued)

*Primary Examiner* — Orlando E Aviles
*Assistant Examiner* — Robert F Neibaur
(74) *Attorney, Agent, or Firm* — Nixon & Vanderhye P.C.

(57) ABSTRACT

A tool for use with a fastener, more particularly, a medical screwdriver tool arranged to interact with a fastener has a driver body with a driver shaft, the driver shaft being associated with a tip configured for interaction with a fastener. The tool has an actuator arranged for reciprocal movement with respect to a longitudinal axis of the driver shaft between a first position proximal the tip and a second position distal the tip. The tip has first and second portions. The tool is configured for moving the first and second portions from a closed condition to an open condition upon movement of the actuator from the second position to the first position.

15 Claims, 9 Drawing Sheets

PART A                    PART B

(58) Field of Classification Search
CPC ....... B25B 23/105; B25B 13/54; B23P 19/06; A61B 17/8888
USPC .......... 81/442, 443, 444, 448, 436, 438, 455
See application file for complete search history.

(56) References Cited

U.S. PATENT DOCUMENTS

| | | | | |
|---|---|---|---|---|
| 4,078,593 | A * | 3/1978 | Benitz | B25B 23/105 81/443 |
| 4,924,736 | A * | 5/1990 | Bonner | B25B 13/54 81/448 |
| 6,244,141 | B1 | 6/2001 | Han | |
| 6,543,317 | B1 * | 4/2003 | Rinner | B25B 13/06 81/125 |
| 7,226,453 | B2 * | 6/2007 | Chao | A61B 17/7082 606/104 |
| 7,249,544 | B2 * | 7/2007 | Totsu | B25B 15/005 81/448 |
| 8,087,329 | B2 * | 1/2012 | Schumacher | B25B 23/108 606/104 |
| 8,347,768 | B2 * | 1/2013 | Witte | A61B 17/8888 81/442 |
| 2007/0212190 | A1 | 9/2007 | Monday et al. | |
| 2008/0269768 | A1 * | 10/2008 | Schwager | A61B 17/8888 606/104 |
| 2009/0211412 | A1 | 8/2009 | Witte | |
| 2013/0150864 | A1 | 6/2013 | Marik et al. | |

OTHER PUBLICATIONS

Chinese Second Office Action dated Jun. 10, 2020 issued in Chinese Patent Application No. 201680078564.4 and English translation, 5 pp.

* cited by examiner

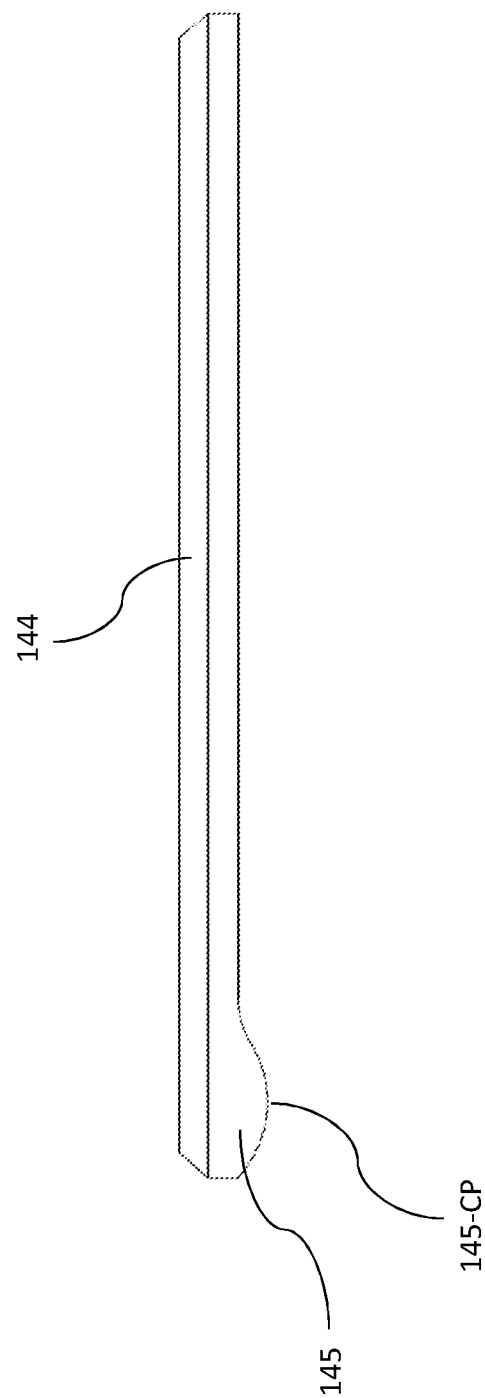

TOOL FOR USE WITH A FASTENER

This application is the U.S. national phase of International Application No. PCT/GB2016/053520 filed Nov. 10, 2016 which designated the U.S. and claims priority to Great Britain Patent Application No. 1519915.1 filed Nov. 11, 2015, the entire contents of each of which are hereby incorporated by reference.

FIELD OF THE INVENTION

The present invention relates to a tool for use with a fastener. More particularly, but not exclusively, the invention relates to tools such as medical screwdrivers arranged to interact with a fastener.

BACKGROUND OF THE INVENTION

A known medical screwdriver is described in US 2009/0211412. Here, the medical screwdriver has a bushing and a shaft with an end split asymmetrically into two parts for clamping a screw. The bushing moves relative to the shaft in a direction either towards or away from the screw to be clamped. The bushing has a contact ring that acts on the outer surface of the shaft. When the bushing is moved towards the split end of the shaft, the pressure from the contact ring onto the shaft is reduced allowing the two parts of the split end of the shaft to move towards each other due to the elasticity of the material of the shaft. This results in a reduction of the clamping force exerted onto the screw by the two parts of the shaft, allowing the screw to come away from the screwdriver. When the bushing is moved away from the split end of the shaft, the contact ring comes in contact with the outer surface of the shaft, and pressure exerted by the contact ring on the shaft causes the two parts of the split end to move away from each other and, in doing so, clamp onto the screw.

This known configuration is problematic when in use. A user of the known screwdriver is likely required to apply a least a small amount of force in the direction of the split end of the shaft nearest the screw in order to secure the screw in a desired position. The act of simultaneously pulling the bushing in a direction away from the screw, whilst also exerting force in the direction of the screw is tricky and counter intuitive in practice. This known configuration also increases the chance of the screw coming away from the screwdriver when the screwdriver is in use, due to the force needed to pull back the bushing on occasions outweighing the general force applied to the shaft to secure the screw in a desired position.

This makes the process of securing a screw with the above known screwdriver tedious, and even dangerous if the screwdriver is used in a medical procedure (e.g. during a hospital operation), because screws may become loose or even lost in the surrounding area of the screw driver.

The present invention seeks to overcome or at least mitigate one or more problems associated with the prior art.

SUMMARY OF INVENTION

According to one aspect of the invention, there is provided a tool for use with a fastener, the tool comprising a driver body having a driver shaft, and an associated tip configured for interaction with a fastener; the tool further comprising an actuator arranged for reciprocal movement with respect to a longitudinal axis of the driver shaft between a first position proximal the tip and a second position distal the tip; wherein the tip comprises first and second portions, and wherein the tool is configured for moving said first and second portions from a closed condition to an open condition upon movement of the actuator from said second position to said first position.

Advantageously, the invention allows for a user to intuitively operate the tool by pushing the actuator forward in the direction of a desired fastener in order to attach a fastener to the tool. This movement is compatible with the direction of force required to use the tool to secure a fastener in a desired place. The invention therefore provides a more reliable and safer way of securing a fastener in a desired place than is currently possible with the tool of US 2009/0211412, and greatly reduces the risk of losing the fastener when the tool is in use.

In an exemplary embodiment, the driver shaft may define the tip.

In exemplary embodiments, the length of the driver body is between 80 mm and 120 mm. In further exemplary embodiments, the width of the driver body is between 4 mm and 10 mm. In a further exemplary embodiment, the width of the driver body is between 4 mm and 10 mm for the majority of the length of the driver body. The above dimensional features improve the overall ergonomics of the tool making it easier for a user to put the tool into use and also provide improved visibility of a fastener on the tip of the driver body when using the tool.

In exemplary embodiments, the actuator is configured to drive against the driver shaft.

In exemplary embodiments, the actuator is configured to drive against a cam profile on the driver shaft. More specifically, the cam profile may comprise a surface on each of the first and second portions wherein the cam profile is configured for enabling movement of the first and second portions with respect to one another during reciprocal movement of the actuator.

This feature of such embodiment is advantageous in that the interaction between the cam profile and the actuator when the actuator moves towards the tip of the driver body causes the movement of the first and second portions of the tip in order for the tool to retain a fastener.

In an exemplary embodiment, the actuator comprises drive projections configured to engage with the cam profile upon movement of the actuator towards the first position. In exemplary embodiments, the actuator comprises drive projections located on opposite sides of the actuator so that the two drive projections face one another.

The use of such projections in exemplary embodiments allows for efficient use of material when forming the tool thus achieving a reduced cost of manufacture.

In exemplary embodiments, the drive projections extend in a direction parallel to the longitudinal axis of the driver shaft. In exemplary embodiments, the drive projections extend in the direction of the first position. In exemplary embodiments, the drive projections extend in the same plane as the actuator.

In exemplary embodiments, an upper surface of each drive projection interacts with an upper part of the cam profile and a lower surface of the said drive projection interacts with a lower part of said cam profile. In exemplary embodiments, the upper surface of each drive projection interacts with the upper part of the cam profile at the same time as the lower surface of the said drive projection interacts with the lower part of said cam profile This feature of such embodiments has the effect of each drive projection applying a uniform force to the first and second portions (by the upper and lower parts of the cam profile, respectively) and easily causing the first and second portions to move apart at the same rate.

The cam profile may be defined by grooves on the driver shaft.

The use of grooves engaging with drive projections has the effect of providing a guide for movement of the actuator by a user and avoids misalignment of the actuator on the drive shaft. This means that the actuator can be easily received by the driver shaft and as a result, the user is assisted by the grooves when using the tool.

In exemplary embodiments, the cam profile defines a taper. In exemplary embodiments, the cam profile comprises a length extending toward the first position, wherein the width of the cam profile decreases as the length of the cam profile increases. In exemplary embodiments, the length of the cam profile is in the range of 5 mm to 25 mm. In further embodiments, the length of the cam profile is in the range of 10 mm to 20 mm. In further embodiments, the length of the cam profile is in the range of 12 mm to 18 mm. In further embodiments, the length of the cam profile is in the range of 14 mm to 16 mm. It will be appreciated that the achievement of the open condition of the first and second portions occurs when the drive projections are received by the tapered cam profile, and in doing so force the first and second portions apart upon movement of the actuator from a second position to a first position. The reduction of width of the cam profile (i.e. the tapering) has the effect of allowing the tool to be compatible with different sized fasteners (e.g. to take account of manufacturing tolerances). Advantageously, the drive projections need not be fully received by the cam profiles (i.e. groove) for the open condition to be achieved. For example, for the tool to engage with a fastener having a head of larger width, the first and second portions will be required to move a larger distance apart (i.e. the drive projection will be required to be more fully received) before interaction with the fastener occurs. In contrast, if the tool is required to engage with a fastener having a head of smaller width, the first and second portions will have less distance to move before the fastener interacts with said first and second portions.

In an exemplary embodiment, the driver shaft defines grooves in an outer surface thereof for cooperation with the drive projections on said actuator (i.e. in order to move the first and second portions from a closed condition to an open condition, or vice versa).

In exemplary embodiments, each groove may define a taper for engagement by the drive projections. In addition, each groove may comprise a length extending toward the first position wherein the width of each groove may decrease as the length of each groove increases. In exemplary embodiments, the length of the driver shaft comprising the groove is in the range of 5 mm to 25 mm. In further embodiments, the length of the driver shaft comprising the cam profile is in the range of 10 mm to 20 mm. In further embodiments, the length of the driver shaft comprising the cam profile is in the range of 12 mm to 18 mm. In further embodiments, the length of the driver shaft comprising the cam profile is in the range of 14 mm to 16 mm.

In exemplary embodiments, the configuration of the taper of the groove is of a gentle gradient (e.g. up to 45°) which provides a tool that can interact with a variety of slightly different sized fasteners. The effect of the length of the groove, together with the gentle gradient of the groove, means the first and second portions are capable of different levels of spacing between being fully together or fully apart, which leads to a tool that is versatile and is applicable to a more diverse range of fastener dimensions.

In exemplary embodiments, the actuator defines a sleeve on said shaft.

In an exemplary device, the actuator comprises at least one release projection and the outer surface of the driver shaft comprises at least one formation for cooperation with the at least one release projection on said actuator, for moving said first and second portions from an open condition to a closed condition upon movement of the actuator from said first position to said second position. In exemplary embodiments, the driver shaft comprises two of said formation. In exemplary embodiments, the two formation are spaced 180 degrees apart. In exemplary embodiments, the actuator comprises two release projections. In exemplary embodiments, the release projections are located 180 degrees apart with respect to the longitudinal axis of the actuator. In exemplary embodiments, the drive projections are located 90 degrees away from the release projections with respect to the longitudinal axis of the actuator.

This feature of such an embodiment allows for the easy transition of the first and second portions from the open condition to the closed position. Since the formation is located on the outer surface of the driver shaft and interacts with the release projections, the user is required only to perform a simple linear movement of the actuator to place the first and second portions in the closed position. This simplicity allows for the use of the tool to be intuitive to a user. In addition, the use of separate release projections to the drive projections means that the corresponding formation and the groove features of the driver shaft can be implemented on the same tool.

In exemplary embodiments, the actuator defines a central axis and the at least one release projection comprises a pin extending radially with respect to said central axis. The pin advantageously facilitates the cooperation of the formation and the at least one release projection and thus helps in achieving the closed condition of the first and second portions.

In exemplary embodiments, the actuator comprises a hold. In a further embodiment, the hold is located on the outer surface of the actuator. In a further embodiment, the hold is in the form of a circular edge protruding radially away from the central axis of the actuator. This feature of such an embodiment allows a user to easily move the actuator to a desired position using their hand or fingers.

Beneficially, the pin may define a curved profile for engagement with the at least one formation. In exemplary embodiments, the at least one formation comprises a ramp. In exemplary embodiments, the at least one formation comprises a ridge. In exemplary embodiments, the ridge is at the top of the ramp. In exemplary embodiments, the ramp engages with the curved profile of said pin upon movement of the actuator to the second position wherein the engagement of said ramp and said curved profile of said pin moves the first and second portions to said closed position. This feature of such an embodiment, avoids jerky and abrupt motion of the actuator and instead provides fluid and continuous movement of the actuator giving a user-friendly easy way of operating the tool.

In exemplary embodiments, the first and second portions comprise first and second cross sections, respectively, and wherein each of the first and second portions comprise edge abutment surfaces, wherein the edge abutment surfaces form part of the perimeter of said first and second cross sections, further wherein the abutment surfaces are configured to engage with a fastener.

In exemplary embodiments, the first and second cross-sections are arranged in such a way that they are configured to form a generally hexagonal face at said tip in said open condition. The generally hexagonal face may be a regular hexagon at said tip in said closed condition. Advantageously, this feature stops spinning of the fastener on the tip of the tool.

In exemplary embodiments, the tool comprises a slot extending between the first portion and the second portion of the tip. In exemplary embodiments, the length of the slot is more than a third of the length of the driver body. In another exemplary embodiment, the length of the slot is more than half the length of the driver body. In a further embodiment the length of the slot is between 10 mm and 90 mm. In further embodiments the length of the slot is between 20 mm and 60 mm. In further embodiments the length of the slot is between 30 mm and 50 mm. In further embodiments the length of the slot is between 35 mm and 45 mm. In further embodiments the length of the slot is 39 mm. In exemplary embodiments, the width of the slot is between 0.1 mm and 1 mm. In further embodiments, the width of the slot is between 0.2 mm and 0.5 mm. In further embodiments, the width of the slot is between 0.25 mm and 0.35 mm. In further embodiments, the width of the slot is 0.3 mm. The slot contributes to beneficial flexing in the driver shaft component of the tool, which allows for either the gripping or release of a fastener. For example, the flexing of the driver shaft creates pressure on a fastener, thus, allowing the fastener to be gripped by the tool. The length of the slot results in a lessening of force required by the drive projections of the actuator to push the first and second portions apart. In exemplary embodiments, the material lost when creating the slot is added to the edge abutment surfaces of each of the first and second portions to ensure that a regular hexagon face can be achieved by the first and second cross sections when the first and second portions are in a closed condition. As previously discussed, the formation of a regular hexagon shape by the first and second portions when in a closed condition ensures that a fastener does not spin on the tip of the tool when the first and second portions are in either of the closed or open conditions.

Most In exemplary embodiments, the first and second portions are configured to secure a fastener when the first and second portions are in the open condition.

In a further embodiment a shoulder is located on the internal wall of the actuator wherein the shoulder defines an area of the internal wall of the actuator that has a smaller diameter. In exemplary embodiments, the shoulder is located at the end of the actuator comprising the drive projections. Optionally, the shoulder extends around the full perimeter of the internal wall of the actuator. The shoulder eradicates significant movement between the driver shaft and actuator when the tool is in use. The shoulder feature also means the actuator is easier to manufacture because it is easier to control the tolerance of a small portion of the actuator.

In exemplary embodiments, the tool comprises a handle, wherein the handle is configured to attach to the distal end of the driver shaft. This feature allows the tool to easily be a handheld device.

BRIEF DESCRIPTION OF THE DRAWINGS

Embodiments of the invention will now be described with reference to the accompanying drawings, in which:

FIG. 6b is a cross sectional view of the one release projection of FIG. 6a.

DETAILED DESCRIPTION OF EMBODIMENT(S)

Figure 1:
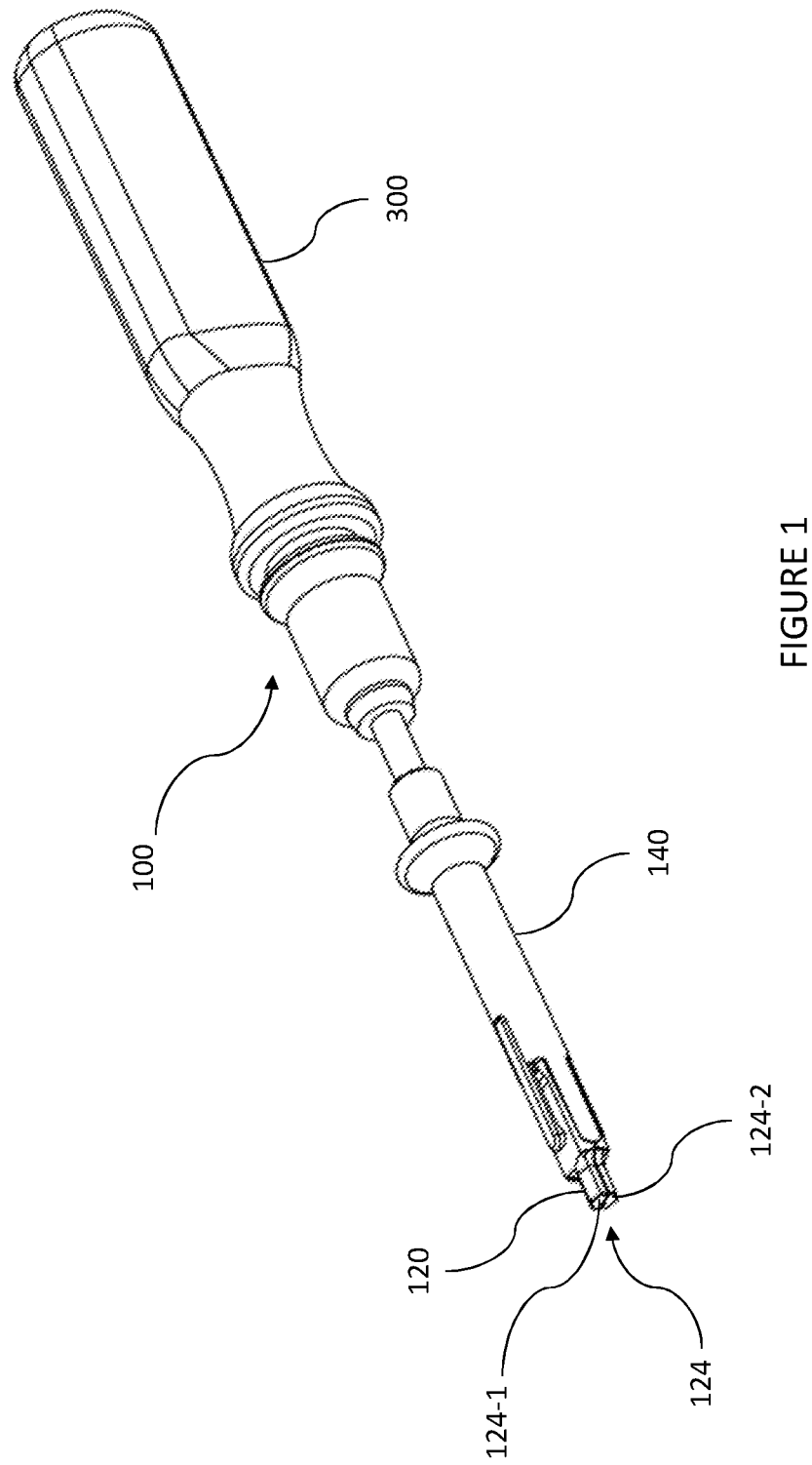
FIG. 1 is a perspective view of a tool for use with a fastener, according to an embodiment of the invention.
Figure 2:
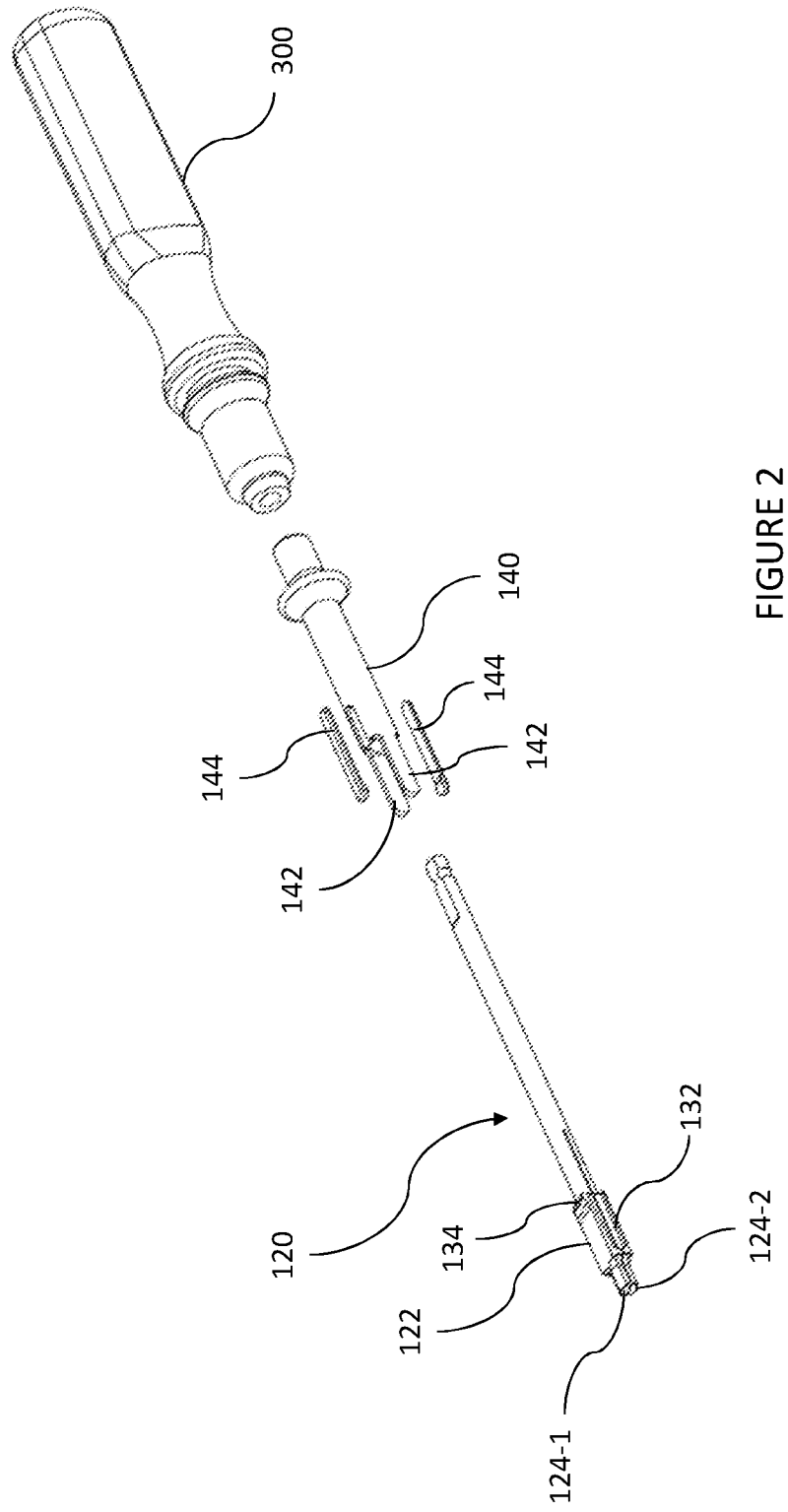
FIG. 2 is an exploded view of the tool of FIG. 1.

Referring firstly to FIGS. 1 and 2, a tool for use with a fastener is indicated generally at 100.

With particular reference to FIG. 1, the tool 100 includes a handle 300 and has a driver body 120 with a driver shaft 122. The driver shaft 122 has an associated tip 124 for interacting with a fastener. In the particular embodiment of FIG. 1, the driver shaft 122 defines the tip 124. The tip 124 has a first portion 124-1 and a second portion 124-2. The tool also has an actuator 140 arranged for reciprocal movement with respect to a longitudinal axis of the driver shaft 122 between a first position proximal the tip 124 and a second position distal the tip 124. The actuator defines a sleeve on the driver shaft 122.

Figure 3:
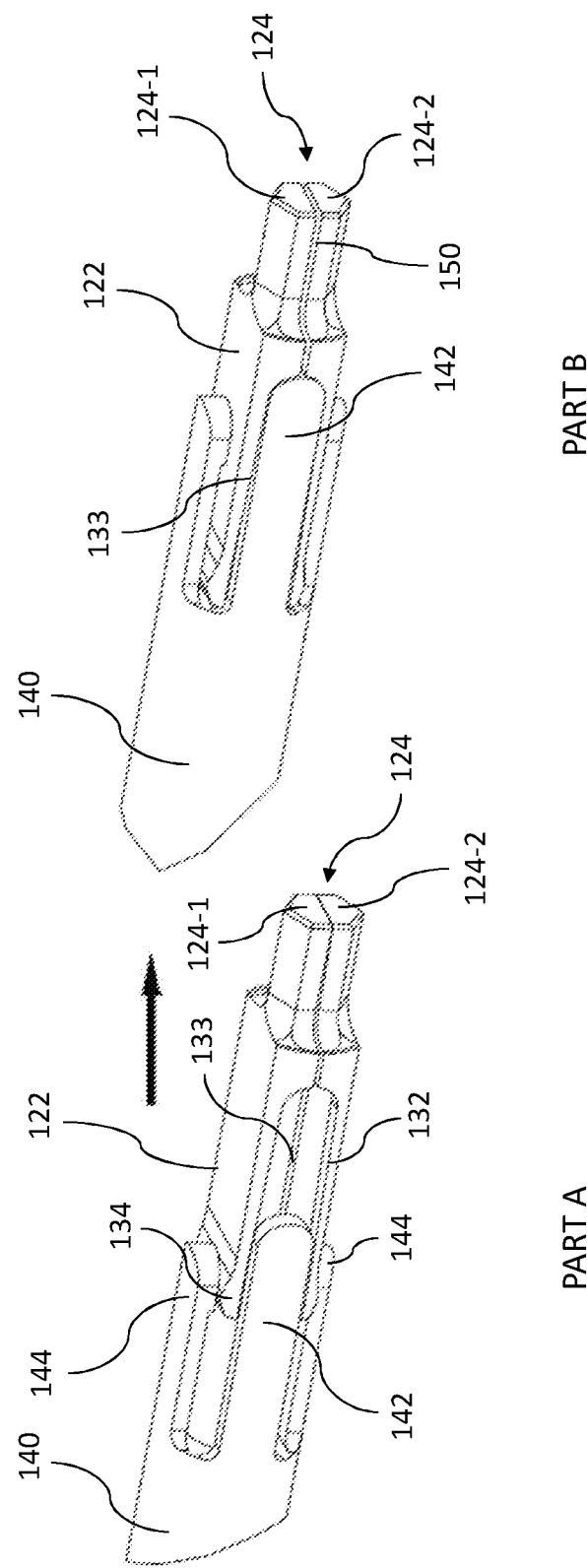
FIG. 3 is a close-up front perspective view of the tool of FIG. 1.

The tool 100 is configured for moving the first portion 124-1 and the second portion 124-2 from a closed condition to an open condition upon movement of the actuator 140 from the second position to the first position (shown in detail in FIG. 3). The tip 124 is configured to secure a fastener when the first and second portions 124-1, 124-2 are in the open condition.

Advantageously, by configuring the tool in the way illustrated, the direction of movement of the actuator required to move the first portion 124-1 and second portion 124-2 into an open position (with the tip interacting with a fastener) allows for a user to intuitively operate the tool by pushing the actuator forward in the direction of the desired fastener in order to attach the fastener to the tool. This movement is compatible with the direction of force required to use the tool to secure the fastener in a desired place. The invention therefore provides a more reliable and safer way of securing a fastener in a desired place and greatly reduces the risk of losing the fastener when the tool is in use.

Looking now to FIG. 2, an exploded view of the tool 100 of FIG. 1 is shown. The driver shaft 122 has a cam profile 132 and a formation 134. The cam profile 132 is a surface on each of the first and second portions 124-1, 124-2. The actuator 140 is configured to drive against the driver shaft 122, in particular, the cam profile 132. More specifically, actuator 140 has drive projections 142 configured to engage with the cam profile 132. Conveniently, the interaction between the cam profile 132 and the actuator 140, and specifically the drive projections 142, when the actuator 140 is moved in a direction towards the tip 124, causes the movement of the first and second portions 124-1, 124-2 of the tip 124 to an open condition in order for the tool 100 to retain a fastener. Using projections, such as drive projections 142, allows for efficient use of material when forming the tool 100, thus, achieving a reduced cost of manufacture. In addition, the upper surface of each drive projection 142 interacts with the upper surface of a corresponding cam profile 132 and the lower surface of said drive projection 142 interacts with the lower surface of said corresponding cam profile 132. These interactions are designed to occur at the same time by the symmetrical configuration of the drive projection 142 and this means that each drive projection 142 applies a uniform force to the first and second portions 124-1, 124-2 and easily causes the first and second portions 1241, 124-2 to move apart at the same rate.

The actuator 140 also has release projections 144 that cooperate with the formation 134 of the driver shaft 122 to move the first portion 124-1 and the second portion 124-2 from an open condition to a closed condition upon movement of the actuator 140 from said first position proximal the tip 124 to said second position distal the tip 124. This relationship is described in more detail below with reference to FIG. 3.

Referring to FIG. 3, Part A shows first portion 124-1 and second portion 124-2 in a closed condition. The cam profile 132 is defined by a tapered groove 133 on the outer surface of the driver shaft 122. The tapered groove 133 reduces in width as the groove 133 extends towards a position proximal the tip 124. The gentle gradient of the taper of the groove 133 provides a tool 100 that is not limited to interacting with a predetermined size of fastener, and instead, can interact with a variety of slightly different sized fasteners. One of the drive projections 142 is shown to be partially engaged with the groove 133. A release projection 144 is in cooperation with the formation 134 of the driver shaft 122. This cooperation firmly holds the first portion 124-1 and the second portion 124-2 in the closed position and allows for an easy transition of the first and second portions from the open condition to the closed position. The location of the formation 134 on the outer surface of the driver shaft 122 means a user is required only to perform a simple linear movement of the actuator 140 away from the tip 124 to place the first and second portions in the closed position. This simplicity allows for the use of the tool 100 to be intuitive to a user. In addition, the use of the separate release projections 144 means that the formation 134 and the groove 133 of the driver shaft 122 can be implemented on the same tool 100.

Part B of FIG. 3 shows first portion 124-1 and second portion 124-2 in an open condition. A slot 150 extends between the first portion 124-1 and the second portion 124-2 and along a length of the driver shaft 122. In exemplary embodiments, the slot has a width of 0.3 mm, however in a further embodiment the width of the slot may be between 0.1 mm and 1 mm. More specifically, in a further embodiment, the width of the slot may be between 0.2 mm and 0.5 mm. In an exemplary embodiment, the width of the slot may be between 0.25 mm and 0.35 mm. The actuator 140 has been moved from a second position distal the tip 124 (see Part A) to a first position proximal the tip 124 (the direction is denoted by the black arrow). In this example, the one drive projection 142 is fully retained by the tapered groove 133 and is, thus, fully engaged with the tapered groove 133. The engagement between the drive projections 142 and the corresponding grooves 133 guides the movement of the actuator 140 on the driver shaft 122 and avoids misalignment of the actuator 140 on the driver shaft 122. This engagement, illustrated in Part B of FIG. 3, places the first portion 124-1 and the second portion 124-2 in an open condition. Advantageously, the tapering of the groove 133 allows the tool 100 to engage with different sized fasteners due to the decreasing width of the taper allowing the first and second portions 124-1 and 124-2 to be forced apart to different distances dictated by the position of the drive projection 142 in the groove 133, wherein the position of the drive projection 142 in the groove 133 is dictated by the size of the fastener to be attached, and more specifically, the size of the head of the fastener.

Figure 4:
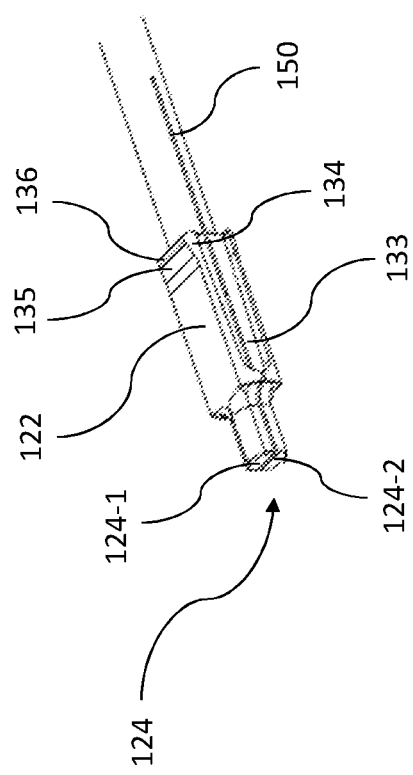
FIG. 4 is a close-up perspective view of the driver shaft feature of the tool of FIG. 1.

Looking now to FIG. 4, the driver shaft 122 is shown in closer detail with the slot 150 separating the first portion 124-1 and the second portion 124-2 of the tip 124 from one another. The formation 134 has a ramp 135 and a ridge 136, wherein the ridge 136 is at the top of the ramp 135. When the first and second portions 124-1, 124-2 are in a closed condition, the release projection 144 of FIG. 3 would cooperate with the ramp 135 of the formation 134. The ridge 136 acts as an abutment to stop the actuator 140 moving unnecessarily down the driver shaft 122. This keeps the actuator 140 in an easily accessible area for the user.

Figure 5:
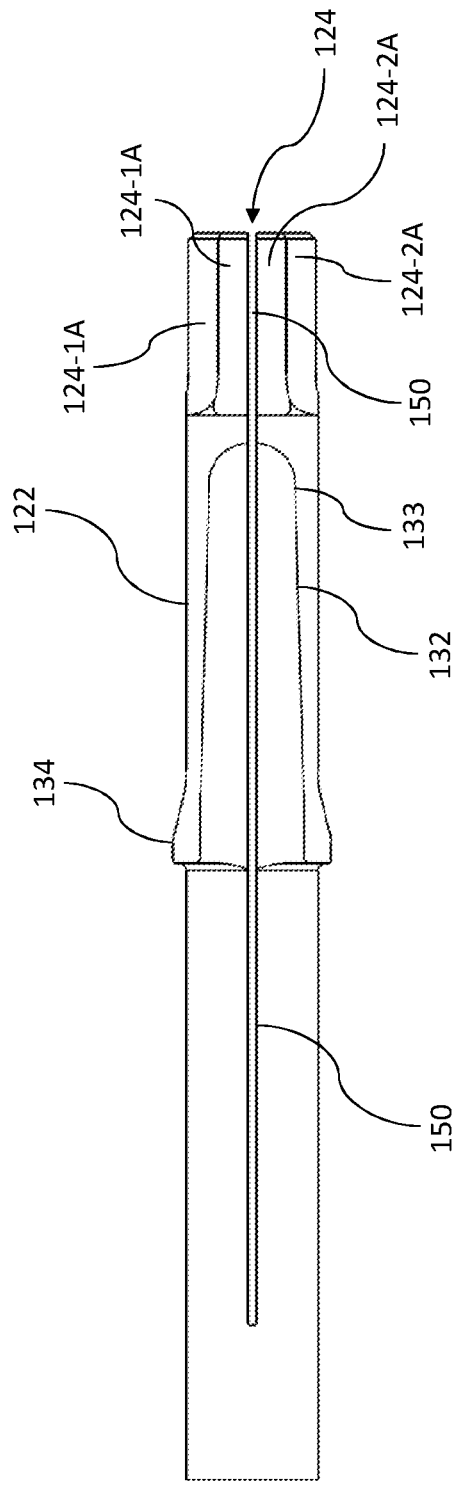
FIG. 5 is a cross sectional view of the driver shaft feature of FIG. 4.

FIG. 5 shows a cross sectional view of the driver shaft 122. The taper of the cam profile 132 defined by groove 133 is shown. Slot 150 extends for over half the length of the driver shaft 122. The first and second portions have first edge abutment surfaces 124-1A and second edge abutment surfaces 124-2A, respectively, wherein the edge abutment surfaces 124-1A, 124-2A form a portion of the perimeter of each cross section of the respective portion, and wherein the edge abutment surfaces 124-1A, 124-2A are configured to engage with a fastener. More detail regarding the cross sections is given later in relation to FIG. 7.

Figure 6A:
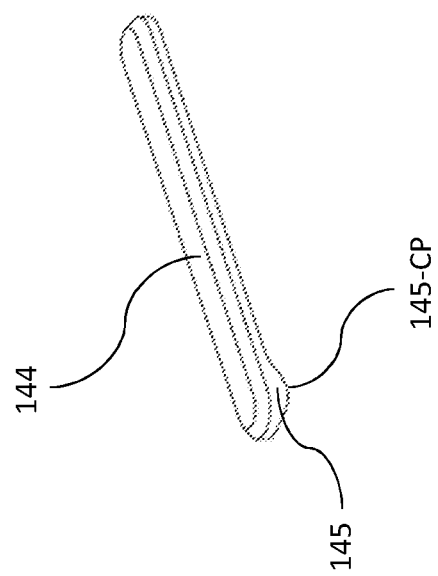
FIG. 6a is a perspective view of one of the release projections of the tool of FIG. 2.

FIG. 6a shows a release projection 144 with a pin 145 having a curved profile 145-CP. When incorporated as part of the tool 100, (e.g. as shown in FIGS. 2 and 3), the pin 145 extends radially in the direction of the central axis of the actuator 140. Each pin 145 of each of the release projections 144 advantageously facilitates the cooperation of the formation 134 with said release projection 144 and thus helps to achieve the closed condition of the first and second portions 124-1, 124-2. The curved profile 145-CP avoids jerky and abrupt motion of the actuator 140 and instead provides fluid and continuous movement of the actuator 140 giving a user-friendly easy way of operating the tool 100. FIG. 6b shows the cross section of the pin 145 of FIG. 6b.

Figure 7:
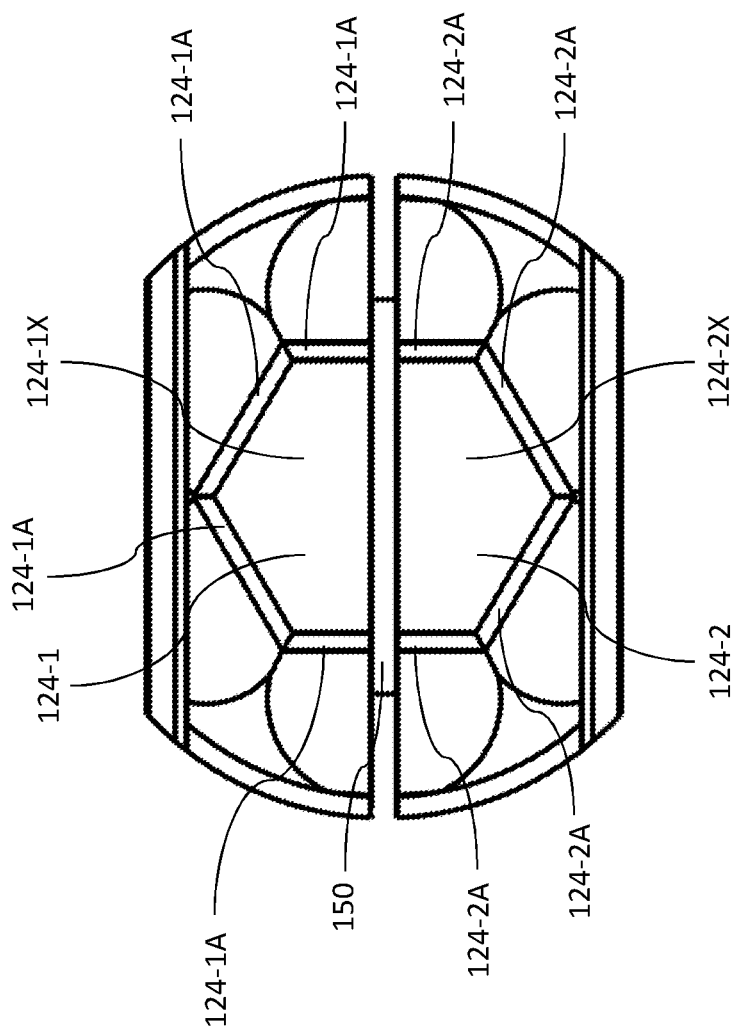
FIG. 7 is a cross sectional view of the tip of the tool of FIG. 1.

Looking now to FIG. 7, the cross section of the tip 124 is shown. The first portion 124-1 has a first cross-section 124-1X with a portion of the perimeter of the first cross section formed by the first edge abutment surfaces 124-1A and the second portion 124-2 has a second cross-section 124-2X with a portion of the perimeter of the second cross section formed by the second edge abutment surfaces 124-2A. The edge abutment surfaces 124-1A, 124-2A are configured to engage with a fastener.

The first and second portions 124-1, 124-2 are in said open condition with slot 150 visible. The first and second cross-sections 124-1X, 124-2X are arranged to form a generally hexagonal face. The material removed to form slot 150 is distributed evenly onto the edge abutment surfaces 124-1A, 124-2A of the first portion 124-1 and the second portion 124-2 so that when the first portion 124-1 and the second portion 124-3 are in a closed position the first and second cross sections 124-1X, 124-2X form a regular hexagon shape. The regular hexagon shape stops spinning of a fastener on the tip 124 of the tool 100.

Figure 8:
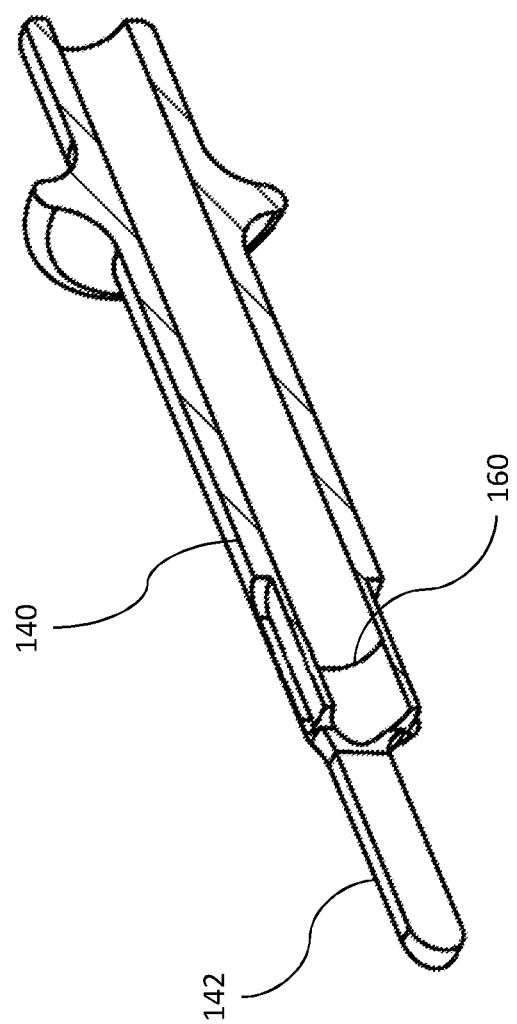
FIG. 8 is a perspective cut away view of the actuator 140 of the tool of FIG. 1 in a further embodiment of the invention.

FIG. 8 shows a perspective view of a cut away of the actuator 140 in a further embodiment of the invention. The actuator has a drive projection 142 and an internal wall with a shoulder 160. The shoulder defines an area of the internal wall of the actuator 140 that has a smaller diameter. In the embodiment of FIG. 8, the shoulder 160 is located at the end of the actuator 140 comprising the drive projections 142.

The shoulder 160 eradicates significant movement between the driver shaft 122 and actuator 140 when the tool 100 is in use. Incorporating the shoulder 160 into the actuator 140 in the way shown in FIG. 8, means the actuator 140 is easier to manufacture because it is easier to control the tolerance of a small portion of the actuator 140.

Throughout the description and claims of this specification, the singular encompasses the plural unless the context otherwise requires. In particular, wherein the indefinite article is used, the specification is to be understood as contemplating plurality as well as singularity, unless the context requires otherwise.

Features, integers, characteristics or compounds described in conjunction with a particular aspect, embodiment or example of the invention are to be understood as being applicable to any other aspect, embodiment or example described herein unless incompatible herewith.

The invention claimed is:

1. A tool for use with a fastener, the tool comprising a driver body having a driver shaft, said driver shaft being connected with a tip configured for interaction with a fastener;
   the tool further comprising an actuator arranged for reciprocal movement with respect to a longitudinal axis of the driver shaft between a first position proximal the tip and a second position distal the tip;
   wherein the tip comprises first and second portions, wherein the tool is configured for moving said first and second portions from a closed condition to an open condition upon movement of the actuator from said second position to said first position, wherein the actuator is configured to drive against a cam profile defined by grooves on the driver shaft, wherein the grooves on the driver shaft are formed in an outer surface of the driver shaft for cooperation with drive projections on said actuator in order to move the first and second portions from a closed condition to an open condition, or vice versa, wherein each groove defines a taper for engagement by a corresponding one of the drive projections, wherein each groove comprises a length extending toward the first position, and wherein the width of each groove decreases as the length of each groove increases.

2. The tool according to claim 1, wherein the actuator defines a sleeve around said drive shaft.

3. The tool according to claim 1, wherein the cam profile comprises a surface on each of the first and second portions, and wherein the cam profile is configured for enabling movement of the first portion with respect to the second portion and enabling movement of the second portion with respect to the first portion during reciprocal movement of the actuator.

4. The tool according to claim 1, wherein the actuator comprises drive projections configured to engage with the cam profile on the driver shaft upon movement of the actuator towards the first position.

5. The tool according to claim 4, wherein the drive projections extend in a direction parallel to the longitudinal axis of the driver shaft.

6. The tool according to claim 1, wherein the cam profile defines the taper.

7. The tool according to claim 6, wherein the cam profile comprises a length extending toward the first position, and wherein the width of the cam profile decreases as the length of the cam profile increases.

8. The tool according to claim 1, wherein the actuator comprises at least one release projection and wherein the outer surface of the driver shaft comprises at least one formation for cooperation with the at least one release projection on said actuator, wherein the formation is configured for moving said first and second portions from the open condition to t closed condition upon movement of the actuator from said first position to said second position.

9. The tool according to claim 8, wherein the actuator defines a central axis, and wherein the at least one release projection comprises a pin extending radially with respect to said central axis.

10. The tool according to claim 9, wherein the pin defines a curved profile for engagement with the at least one formation.

11. The tool according to claim 1, wherein the first and second portions comprise first and second cross sections, respectively, and wherein each of the first and second portions comprise edge abutment surfaces, wherein the edge abutment surfaces form part of the perimeter of the cross section of the respective portion, further wherein the abutment surfaces are configured to engage with a fastener upon movement of the actuator to said first position.

12. The tool according to claim 11, wherein the first cross-section and the second cross-section are arranged in such a way that they are configured to form a hexagonal face at said tip in said open condition.

13. The tool according to claim 1, wherein the tool comprises a handle, wherein the handle is configured to attach to the distal end of the driver shaft.

14. The tool according to claim 1, wherein the tool comprises a slot extending between the first portion and the second portion of the tip.

15. The tool according to claim 1, wherein the actuator comprises an internal wall with a shoulder.

* * * * *